(12) United States Patent
Govari et al.

(10) Patent No.: US 10,416,247 B2
(45) Date of Patent: Sep. 17, 2019

(54) SINGLE AXIS SENSORS ON FLEXIBLE BACKBONE

(71) Applicant: BIOSENSE WEBSTER (ISRAEL) LTD., Yokneam (IL)

(72) Inventors: Assaf Govari, Haifa (IL); Andres Claudio Altmann, Haifa (IL); Jennifer Maffre, Pasadena, CA (US); Maribeth Wilczynski, Glendale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 462 days.

(21) Appl. No.: 14/285,667

(22) Filed: May 23, 2014

(65) Prior Publication Data

US 2014/0317910 A1    Oct. 30, 2014

Related U.S. Application Data

(62) Division of application No. 12/186,631, filed on Aug. 6, 2008, now Pat. No. 8,926,528.

(51) Int. Cl.
*G01R 33/34* (2006.01)
*A61B 5/00* (2006.01)
(Continued)

(52) U.S. Cl.
CPC ........ *G01R 33/34084* (2013.01); *A61B 5/062* (2013.01); *A61B 5/065* (2013.01); *A61B 5/6859* (2013.01); *A61B 34/20* (2016.02); *A61M 25/0127* (2013.01); *A61B 2034/2051* (2016.02); *A61B 2034/2072* (2016.02);
(Continued)

(58) Field of Classification Search
CPC ... A61B 5/065; A61B 5/6859; A61B 19/5244; A61B 2019/5251; A61B 5/06; A61B 5/062; A61M 2025/0166; A61M 25/0127; G01R 33/285; G01R 33/287; G01R 33/34084
See application file for complete search history.

(56) References Cited

U.S. PATENT DOCUMENTS 6,233,476 B1    5/2001  Strommer et al.
6,272,371 B1 *  8/2001  Shlomo .................... A61B 5/06
                                                  128/899
(Continued)

FOREIGN PATENT DOCUMENTS

EP    1504713 A1    2/2005
EP    1484026 B1    3/2007
(Continued)

OTHER PUBLICATIONS

EP Search Report No. EP11178609 dated Jul. 1, 2013.
(Continued)

*Primary Examiner* — Devin B Henson
(74) *Attorney, Agent, or Firm* — Vincent J. Serrao

(57) ABSTRACT

An apparatus includes a narrow elongate probe is adapted for insertion into the body of a living subject. The probe may be flexible and has a plurality of sensors consisting of single coils of very fine wire wound about a backbone of the probe, which transmit signals proximally via fine connecting wires to a position processor. The position processor analyzes the signals to determine position coordinates at multiple points along the length of the probe.

4 Claims, 2 Drawing Sheets

(51) Int. Cl.
*A61B 5/06* (2006.01)
*A61B 34/20* (2016.01)
*A61M 25/01* (2006.01)
*G01R 33/28* (2006.01)

(52) U.S. Cl.
CPC ... *A61M 2025/0166* (2013.01); *G01R 33/285* (2013.01); *G01R 33/287* (2013.01); *Y10T 29/4902* (2015.01)

(56) References Cited

U.S. PATENT DOCUMENTS

| | | | |
|---|---|---|---|
| 6,366,799 B1 | 4/2002 | Acker et al. | |
| 6,374,134 B1 | 4/2002 | Bladen et al. | |
| 6,574,492 B1 | 6/2003 | Ben-Haim et al. | |
| 6,690,963 B2 | 2/2004 | Ben-Haim et al. | |
| 6,961,602 B2 | 11/2005 | Ben-Haim et al. | |
| 7,003,342 B2* | 2/2006 | Plaza | A61B 5/0422 600/374 |
| 7,130,700 B2* | 10/2006 | Gardeski | A61M 25/0021 600/585 |
| 7,555,330 B2 | 6/2009 | Gilboa et al. | |
| 7,561,907 B2 | 7/2009 | Fuimaono et al. | |
| 2001/0047133 A1* | 11/2001 | Gilboa | A61B 5/06 600/429 |
| 2003/0018251 A1 | 1/2003 | Solomon | |
| 2004/0242984 A1 | 12/2004 | Plaza | |
| 2007/0049797 A1* | 3/2007 | Yoshida | A61B 1/00082 600/117 |
| 2007/0232898 A1* | 10/2007 | Huynh | A61B 5/1076 600/424 |
| 2008/0139915 A1* | 6/2008 | Dolan | A61B 5/06 600/407 |
| 2009/0102479 A1* | 4/2009 | Smith | G01R 33/287 324/309 |
| 2009/0299174 A1* | 12/2009 | Wright | A61B 5/06 600/424 |
| 2009/0306651 A1 | 12/2009 | Schneider | |

FOREIGN PATENT DOCUMENTS

| | | |
|---|---|---|
| EP | 1943974 A1 | 7/2008 |
| JP | 2000-508224 | 7/2000 |
| JP | 2005-007167 | 1/2005 |
| WO | WO 96/05768 A1 | 2/1996 |
| WO | WO 97/24983 A2 | 7/1997 |
| WO | WO 98/29033 | 7/1998 |
| WO | WO 00/10456 A1 | 3/2000 |
| WO | WO 08/028149 A2 | 3/2008 |

OTHER PUBLICATIONS

CN Search Report—dated Sep. 11, 2012.
CN First Office Action—dated Sep. 28, 2012.
CN Second Office Action—dated Jun. 24, 2013.
CN Third Office Action—dated Jan. 23, 2014.
CN Fourth Office Action—dated Jul. 28, 2014.
JP Office Action—dated Nov. 5, 2013.
Canadian Examiner's Requisition dated Jul. 18, 2016 from corresponding Canadian Patent Application No. 2,674,225.
European Examination Report dated Feb. 2, 2017 from corresponding European Patent Application No. 11178609.1.

* cited by examiner

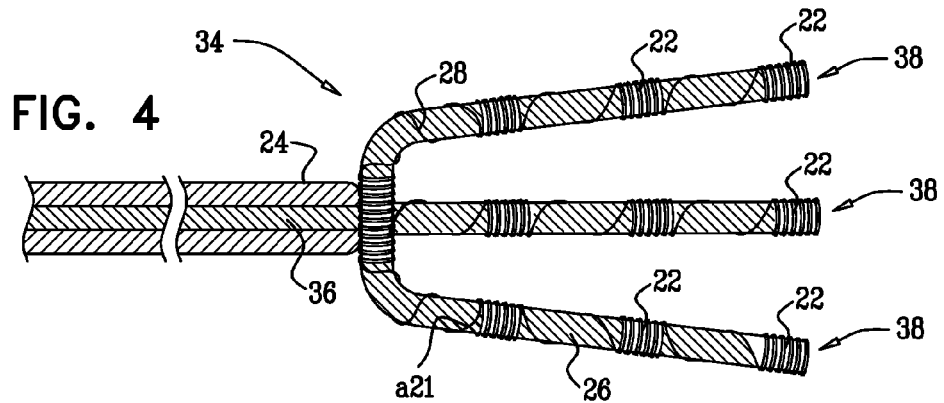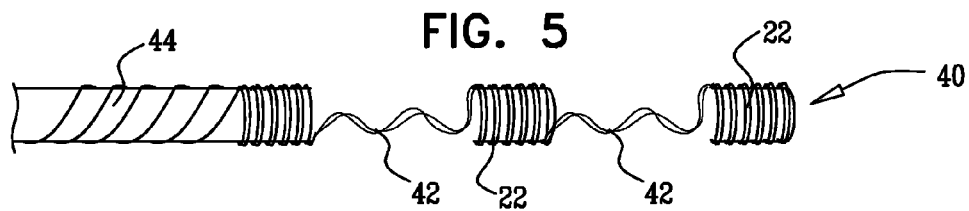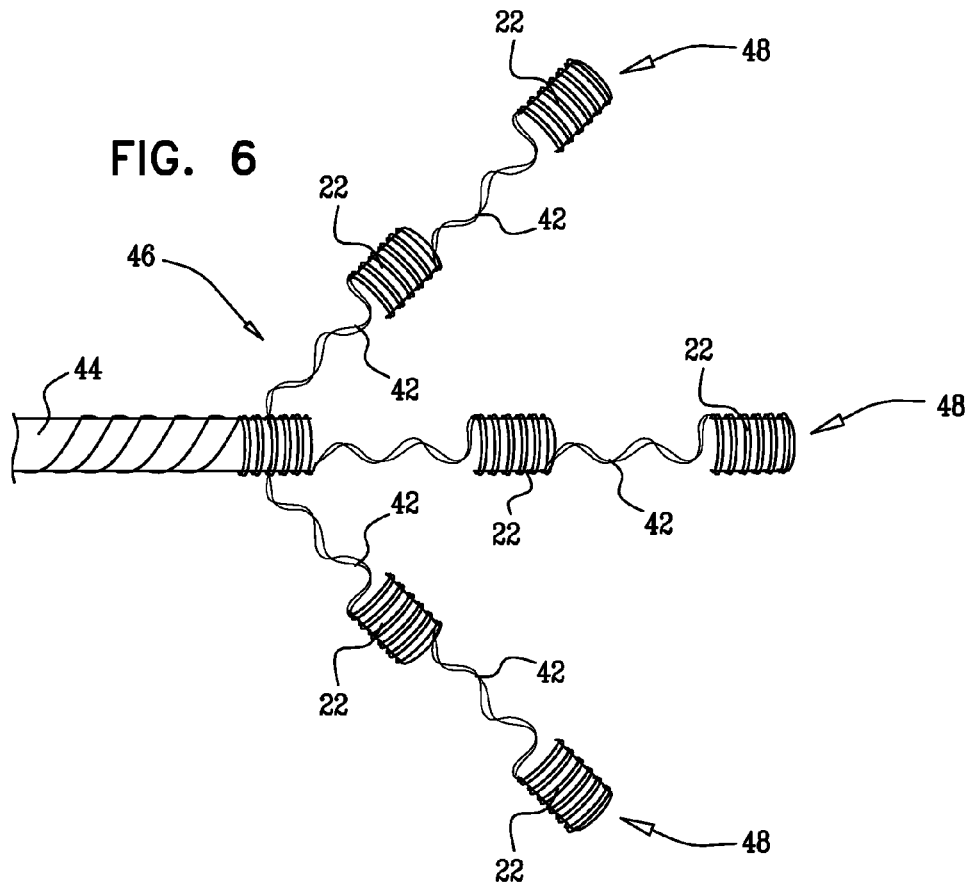

SINGLE AXIS SENSORS ON FLEXIBLE BACKBONE

This Application is a Divisional Patent Application of U.S. patent application Ser. No. 12/186,631 filed Aug. 6, 2008.

BACKGROUND OF THE INVENTION

Field of the Invention

This invention relates to invasive medical devices. More particularly this invention relates to localization of invasive medical probes within the body.

Description of the Related Art

Probes, such as catheters, which are suitable for various medical procedures and internal imaging, are now common. Such probes include angioplasty catheters, catheters with laser, electrical or cryoablation characteristics, catheters having ultrasound imaging heads, probes used for nearly incisionless surgery or diagnosis, and endoscopes.

Where such probes are used for treatment, the probes must be carefully positioned in relation to the body structure. In one application, cardiac catheters comprising electrophysiological sensors are known for mapping the electrical activity of the heart. Typically, time-varying electrical potentials in the endocardium are sensed and recorded as a function of position inside the heart, and then used to map the local electrogram or local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector.

Mapping the activation front and conduction fields aids the physician in identifying and diagnosing abnormalities, such as ventricular and atrial tachycardia and ventricular and atrial fibrillation, that result from areas of impaired electrical propagation in the heart tissue.

Localized defects in the heart's conduction of activation signals may be identified by observing phenomena such as multiple activation fronts, abnormal concentrations of activation vectors, or changes in the velocity vector or deviation of the vector from normal values. Furthermore, there may be no electrical propagation at all within defective portions of the heart muscle that have ceased to function, for example, due to local infarction. Once a defect is located by such mapping, it may be ablated (if it is functioning abnormally) or otherwise treated so as to restore the normal function of the heart insofar as is possible.

Mapping of the electrical activation time in the heart muscle requires that the location of the sensor within the heart be known at the time of each measurement. In the past, such mapping was performed using a single movable electrode sensor inside the heart, which sensor measured activation time relative to a fixed external reference electrode. This technique, however, requires calibration, for example impedance calibrations with adjustments for impedance unrelated to that of the body. Mapping of electrical activation time using a single electrode is, furthermore, a lengthy procedure, which must generally be performed under fluoroscopic imaging, thereby exposing the patient to undesirable ionizing radiation. Further, in an arrhythmic heart, activation times at a single location may change between consecutive beats.

Because of the drawbacks of single-electrode mapping, a number of inventors have taught the use of multiple electrodes to measure electrical potentials simultaneously at different locations in the endocardium, thereby allowing activation time to be mapped more rapidly and conveniently, as described. For example, PCT patent publication number WO 97/24983 (Ben-Haim), which is herein incorporated by reference, describes an arrangement wherein three non-collinear electrodes are attached to a substantially rigid ring at the distal end of a catheter, so that the direction of the electrical activation vector in the plane defined by the electrodes may be fully determined.

PCT patent publication number WO96/05768, whose disclosure is incorporated herein by reference, describes a position-responsive catheter comprising a plurality of miniature, preferably non-concentric sensor coils fixed in its distal end. Electrical signals generated by these coils in response to an externally applied magnetic field are analyzed to determine, six-dimensional position and orientation coordinates of the coils.

U.S. Pat. No. 6,272,371, issued to Ben-Haim, which is herein incorporated by reference, discloses a plurality of sensors that are fixed to the distal portion of a probe in known positions relative to the distal end, which sensors generate signals responsive to bending of the probe. Signal processing circuitry receives the bend responsive signals and processes them to find position and orientation coordinates of at least the first sensor, and to determine the locations of a plurality of points along the length of the distal portion of the probe.

SUMMARY OF THE INVENTION

As noted in the above-described applications, it is often useful to obtain position measurements from sensors at multiple locations along the length of a catheter or other probe. In many cases, however, the navigation of the probe and measurements are impeded by the size of the position-sensing coils and the need to accommodate the coils in the very part of the probe whose location is to be sensed.

According to disclosed embodiments of the invention, a narrow probe is adapted for insertion into the body of a living subject. The probe may be flexible and has a plurality of sensors consisting of single coils of very fine wire wound about a backbone of the probe, which transmit signals proximally via fine connecting wires to a position processor. The position processor analyzes the signals to determine position coordinates at multiple points along the length of the probe. The probe does not require orthogonal sensing coils nor special calibration procedures, and can be practically produced with smaller diameters than conventional probes. The techniques are applicable to any type of catheter and requirement for determining the position of an electrode.

An embodiment of the invention provides an invasive medical probe apparatus, including an elongate flexible probe, having a distal end adapted for insertion into a body of a subject, and a plurality of coils that are fixed at different, respective points in a known relation to a reference location on the probe. When subjected to an externally applied magnetic field, the coils generate respective signals responsively to position coordinates thereof. The apparatus includes signal processing circuitry, which receives the signals and processes them to determine respective locations of the points along a portion of the probe.

According to one aspect of the apparatus, the coils are supported by flexible connecting wires that attach the coils to the proximal segment of the probe.

According to a further aspect of the apparatus, the distal segment of the probe divides into a plurality of flexible branches, and the coils are distributed on the branches.

According to still another aspect of the apparatus, the coils are formed of wire that has a diameter in a range of 8 to 70 microns.

According to one aspect of the apparatus, the coils are formed of wire that does not exceed 15 microns in diameter.

According to yet another aspect of the apparatus, the coils are formed of wire that does not exceed 10 microns in diameter.

According to an additional aspect of the apparatus, a diameter of the probe does not exceed 8 French.

One aspect of the apparatus the probe has an internal longitudinal backbone, and the coils are spirally disposed about the backbone and carried thereon.

According to still another aspect of the apparatus, the coils are connected to the signal processing circuitry by respective wires running along the backbone.

According to aspect of the apparatus, the backbone is formed of a longitudinally non-perforate material.

According to a further aspect of the apparatus, the backbone includes a ferromagnetic material.

According to yet another aspect of the apparatus, the backbone has a central lumen.

According to still another aspect of the apparatus, the signal processing circuitry is operative to determine translational and orientational coordinates of the coils in six dimensions.

According to an additional aspect of the apparatus, the signal processing circuitry is operative to determine a bend angle of the probe.

According to an additional aspect of the apparatus, the signal processing circuitry is operative to determine a radius of curvature of a distal portion of the probe.

Other aspects of the invention provide a method that is carried out by the above described apparatus.

An embodiment of the invention provides a method of making an invasive medical probe, which is carried out by providing an internal longitudinal backbone for an elongate flexible probe, disposing a plurality of coils about the backbone, wherein the coils are fixed at different, respective points in a known relation to the distal end of the probe. The method is further carried out by attaching respective connecting wires to the coils for connection of the coils to signal processing circuitry, and applying an external layer about the connecting wires and the backbone.

An aspect of the method is carried out by winding the coils about the backbone.

Another aspect of the method is carried out by pre-forming the coils and slipping the pre-formed coils over the backbone.

A further aspect of the method is carried out by dividing the backbone into a plurality of branches, and distributing the coils on the branches.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein:

FIG. 4 illustrates the distal portion of a multi-branched catheter in accordance with an alternate embodiment of the invention;

FIG. 5 illustrates the distal portion of a catheter in accordance with an alternate embodiment of the invention; and FIG. 6 illustrates the distal portion of a multi-branched catheter in accordance with an alternate embodiment of the invention.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Figure 1:
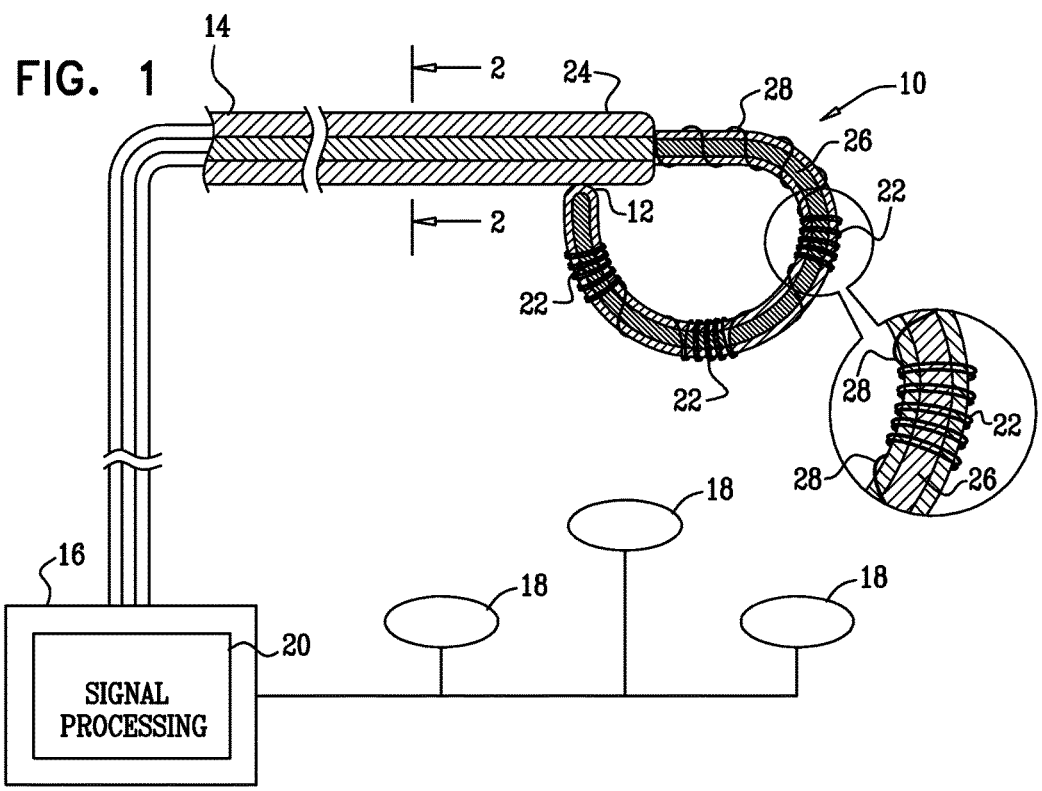
FIG. 1 illustrates a bend-responsive catheter, in accordance with a disclosed embodiment of the invention.

Turning now to the drawings, reference is initially made to FIG. 1, which illustrates a bend-responsive probe or catheter 10, in accordance with a disclosed embodiment of the invention. The catheter 10 includes a distal end 12, which is preferably inserted in the heart of a subject, and a proximal end 14, which is coupled to a control console 16. The catheter 10 may be, for example a LASSO circular mapping catheter, available from Biosense Webster, Inc., 3333 Diamond Canyon Road, Diamond Bar, Calif. 91765, modified in order to apply the principles of the invention.

Adjacent to distal end 12, there are sensors that develop positional signals responsively to magnetic fields. The above-mentioned PCT publication WO96/05768 discloses producing magnetic fields as applied by field generators 18. The sensor signals are conveyed via wires (not shown in FIG. 1) or wirelessly to signal processing and computing circuitry 20 in control console 16, which preferably also provides driver and control signals to field generators 18. Circuitry 20 analyzes the signals, as further described in the above-noted PCT publication, in order to determine six-dimensional translational and orientational coordinates of coils 22 in relation to a frame of reference established by field generators 18. The coils 22 are disposed at known respective locations with respect to a reference point on the catheter 10, for example the distal end 12, or in the case of multi-branched embodiments (described below), a branch point on the body of the catheter 10.

The catheter 10 comprises a conventional outer layer 24, which is applied over an internal flexible backbone 26, which can be, for example, a flexible plastic rod. Alternatively, the backbone 26 may be made of a ferromagnetic material.

Multiple single-axis sensing coils 22 are spirally disposed around and carried by the backbone 26, e.g., by winding them about the backbone 26, and are connected to the circuitry 20 by wires 28. Alternatively, the coils 22 can be preformed, and slipped onto the backbone 26. The coils 22 and connecting wires 28 are formed of wires on the order of 10 microns in diameter. The wires may range from 8 to 70 microns in different applications. The wires 28 preferably spiral about the backbone 26 as they run proximally. As conventional orthogonal coils are not used, the catheter can be less than 8 French (2.7 mm) in diameter. Indeed, using the above-described technique, it is feasible to construct probes having an outer diameter as small as 0.5 mm. When the backbone 26 is made of ferromagnetic material, the gain of the coils 22 is increased.

Each of the coils 22 outputs a signal indicative of its position, relative to the frame of reference of the magnetic fields generated by the field generators 18. Thus, by processing the signals from all the coils 22, the circuitry 20 can track the overall shape and position of the catheter 10 in the body, including the bend angle or the radius of curvature of the distal portion of the catheter 10 at a given time. Structures of interest, such as electrodes may be positioned on the catheter 10 at known fixed locations with respect to at least one of the coils 22, the precise location of such structures can be derived from the coordinates of the coils 22. In a circular lasso catheter, as pictured in FIG. 1, the coils 22 permit the disposition of the entire lasso to be determined relative to structures of interest. This can be done using the methods described in U.S. Pat. No. 6,374,134, issued to Bladen et al., which is herein incorporated by reference. Briefly, in one embodiment, the computation described in U.S. Pat. No. 6,374,134 is performed iteratively for each of the coils 22 by:

1) energizing a single field generating element to establish a field,
2) measuring a value of the field strength at the field sensor, which is dependent on the location and orientation of the sensor within the field,
3) repeating steps 1) and 2) for each field generating element,
4) calculating, by utilizing all the values measured in step 2) and an estimate of the direction of the sensor from the field generator, a direction dependent weighting factor for each field generating element so that calculated field strength B is equal to the field strength B that would exist at the sensor if the axis of the field were directed towards the sensor,
5) iteratively altering the direction dependent weighting factors to maximize B and thus to determine to a desired level of accuracy the direction of the sensor from the field generator, and
6) employing the measured values of the field strength to calculate the distance of the sensor from the field generator and hence, from the direction of the sensor in step 5), the location of the sensor relative to the field generator.

Figure 2:
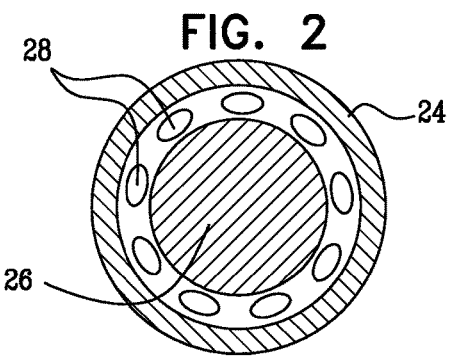
FIG. 2 is a cross sectional view through line 2-2 of the catheter shown in FIG. 1, in accordance with a disclosed embodiment of the invention.

Reference is now made to FIG. 2, which is a cross sectional view through the catheter 10 (FIG. 1) through line 2-2, in accordance with a disclosed embodiment of the invention. The outer layer 24 encloses wires 28, which in turn overlie the backbone 26. In this embodiment, the backbone 26 is formed of a flexible solid longitudinally non-perforate material, i.e., lacking a longitudinal lumen.

Alternate Embodiment 1

Figure 3:
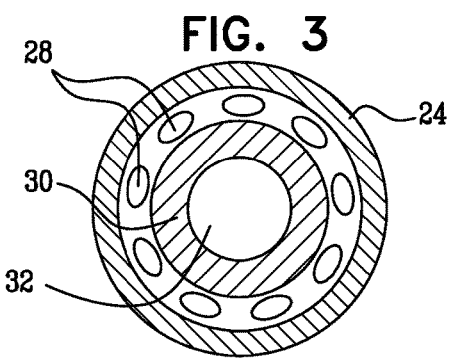
FIG. 3 is a cross sectional view through a catheter in accordance with an alternate embodiment of the invention.

Reference is now made to FIG. 3, which is a cross sectional view through a catheter in accordance with an alternate embodiment of the invention. In this embodiment, the backbone is a hollow tube, comprising a shell 30, and a central lumen 32 that serves as a working channel for the catheter.

Alternate Embodiment 2

Reference is now made to FIG. 4, which illustrates the distal portion of a catheter 34 in accordance with an alternate embodiment of the invention. Like the catheter 10 (FIG. 1), the catheter 34 has a backbone 36, which divides into a plurality of branches 38, each having the same construction as described with respect in the single-branched embodiment of FIG. 1. When suitable electrodes (not shown) are incorporated into the catheter 34, the provision of a large array of coils 22 on multiple branches enables contact mapping to be accomplished quickly, with a high resolution of location information. For example, endocardial surface mapping using the coils 22 on the branches 38 allows rapid identification of an area of interest in which the earliest site of electrical activation can be precisely determined. The branches 38 are constructed so as to be flexible and soft, thus assuring atraumatic contact with target tissue.

Alternate Embodiment 3

Reference is now made to FIG. 5, which illustrates the distal portion of a catheter 40 in accordance with an alternate embodiment of the invention. The distal portion of the catheter 40 is provided with a plurality of coils 22, as in the first embodiment. However, instead of a backbone, the coils 22 are supported by twisted wire pairs 42, which are sturdy enough to support the coils 22, yet flexible. Like the catheter 10 (FIG. 1), the catheter 40 is bend responsive. The wire pairs 42 connect the coils 22 with a proximal segment 44 of the catheter 40 may be constructed of a shape memory alloy, such as nickel-titanium. Alternatively, other materials, such as cobalt chromium, and annealed stainless steel, may be used.

Alternate Embodiment 4

Reference is now made to FIG. 6, which illustrates the distal portion of a catheter 46 in accordance with an alternate embodiment of the invention. The distal portion of the catheter 46 divides into a plurality of branches 48, each being constructed in the same manner as the single-branched catheter 40 (FIG. 5).

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of making an invasive medical probe, comprising the steps of:
   providing an internal longitudinal backbone for an elongate flexible probe, said probe having a distal end;
   disposing a plurality of coils about said backbone, said coils being configured in a non-orthogonal relationship concentric with the backbone, said coils being fixed at different, respective points in a known relation to said distal end, and when subjected to an externally applied magnetic field, said coils being configured to generate respective signals;

attaching respective connecting wires to said coils for connection of said coils to signal processing circuitry, said signal processing circuitry configured to determine the translation and orientational coordinates of the coils in six dimensions; and applying an external layer about said connecting wires and said backbone.

2. The method according to claim 1, wherein disposing a plurality of coils comprises winding said coils about said backbone.

3. The method according to claim 1, wherein disposing a plurality of coils comprises pre-forming said coils and slipping said pre-formed coils over said backbone.

4. The method according to claim 1, further comprising the steps of dividing said backbone into a plurality of branches, and distributing said coils on said branches.

\* \* \* \* \*